United States Patent [19]

Decker

[11] Patent Number: 5,800,401
[45] Date of Patent: Sep. 1, 1998

[54] DISPOSABLE VENOCLYSIS ADAPTOR DEVICE

[75] Inventor: Hubert B. Decker, B. F. Resort Las Pinas, Philippines

[73] Assignee: D.A.D. Ltd., Hong Kong

[21] Appl. No.: 697,651

[22] Filed: Aug. 28, 1996

(Under 37 CFR 1.47)

Related U.S. Application Data

[63] Continuation of PCT/95/00625, Feb. 28, 1994.

[51] Int. Cl.$^6$ ............................................. A61M 5/32
[52] U.S. Cl. .................. 604/174; 604/180; 128/DIG. 26
[58] Field of Search .............................. 604/174, 178, 604/180, 129; 128/DIG. 26

[56] References Cited

U.S. PATENT DOCUMENTS

| | | |
|---|---|---|
| 2,669,231 | 2/1954 | Fisher . |
| 3,726,280 | 4/1973 | Lacount . |
| 4,088,136 | 5/1978 | Hasslinger et al. . |
| 4,096,863 | 6/1978 | Kaplan et al. . |
| 4,416,664 | 11/1983 | Womack . |
| 4,445,894 | 5/1984 | Kovacs . |
| 4,591,356 | 5/1986 | Christie . |
| 4,671,787 | 6/1987 | Widman . |
| 4,702,736 | 10/1987 | Kalt et al. ............... 128/DIG. 26 X |
| 4,966,589 | 10/1990 | Kaufman . |
| 5,019,050 | 5/1991 | Lynn et al. . |
| 5,037,397 | 8/1991 | Kalt et al. . |
| 5,038,778 | 8/1991 | Lott ....................... 128/DIG. 26 X |
| 5,084,026 | 1/1992 | Shapiro . |
| 5,167,650 | 12/1992 | Paul . |
| 5,226,892 | 7/1993 | Boswell ................. 128/DIG. 26 X |
| 5,236,421 | 8/1993 | Becher .......................... 604/180 |
| 5,263,943 | 11/1993 | Vanderbrook . |
| 5,266,401 | 11/1993 | Tollini . |
| 5,449,340 | 9/1995 | Tollini ........................ 604/180 X |
| 5,529,062 | 6/1996 | Byrd ........................... 604/180 X |

*Primary Examiner*—Sam Rimell
*Attorney, Agent, or Firm*—Anderson, Kill & Olick, P.C.

[57] ABSTRACT

A disposable venoclysis adaptor device for supporting a venotube at a person's limb and including at least one flexible fastening strap to be secured at the person's limb, two spacing cushions securable to the strap, an adaptor pillow securable to the strap between the two cushions, an adaptor flap provided between the cushions and cooperating with the adapter pillow for fixedly retaining a venotube therebetween, and a tube flax provided on the fastening strap for securing an extension of the venotube for preventing displacement of the venotube upon person's limb movement.

8 Claims, 1 Drawing Sheet

U.S. Patent    Sep. 1, 1998    5,800,401
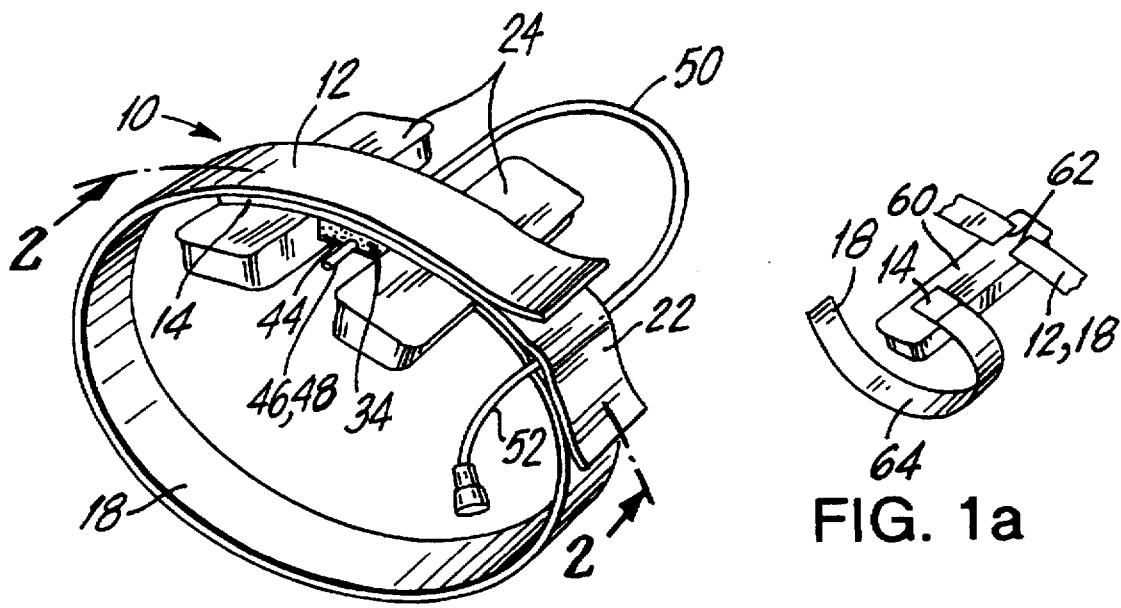
FIG. 1
FIG. 1a
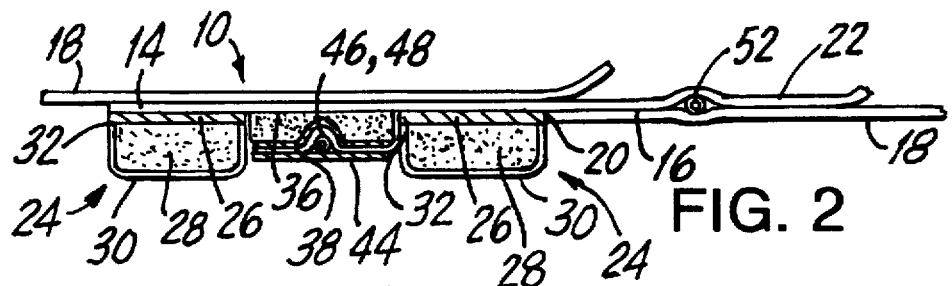
FIG. 2
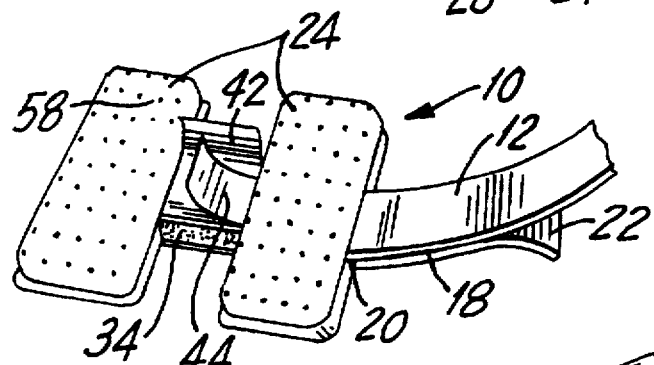
FIG. 3
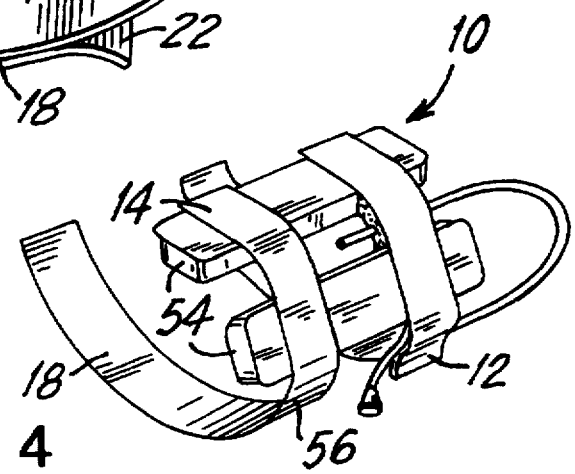
FIG. 4

DISPOSABLE VENOCLYSIS ADAPTOR DEVICE

RELATED APPLICATION

This application is a Continuation of International Application No. PCT/95/00625 filed Feb. 28, 1994 and designating U.S.

BACKGROUND OF THE INVENTION

The instant invention relates generally to venoclysis catheter and intravenous set devices used for intravenous transfusions and, more specifically, to venoclysis and intravenous adaptor devices which securely hold the venetube or butterfly in position.

At the current state of the art, a patient must be restrained of free movement after a venoclysis is applied so that the venetube and/or butterfly remains in place and so that no infiltration, thrombophlebitis, injury to the blood vessel or the surrounding tissue results.

Usually, a venoclysis is applied with the use of medical tapes and splints, which apply pressure on the insertion point and on the patients limb, thereby reducing fluid flow in the blood vessel and giving limited support to the tube against any biasing force.

SUMMARY OF THE INVENTION

It is therefore, a primary object to the present invention to provide a disposable venoclysis adaptor device which securely holds the venetube or the butterfly in position.

A further object of the present invention is to provide a disposable venoclysis adaptor device which relieves the limb from pressure within the insertion point area.

A yet further object of the present invention is to provide a disposable venoclysis adaptor device which permits complete free patients movement while keeping the venetube or butterfly in a fixed position relative to the insertion point without the use of any restraining device.

A yet further object of the present invention is to provide disposable venoclysis adaptor device which adjust to limbs of various diameter at the dorsal or ventral area and keeps the insertion point open for checking.

A yet further object of the present invention is a provide disposable venoclysis adaptor device which is simple to administer and remove and does not irritate the skin or a hairy area.

A yet still further object of the present invention is to provide disposable venoclysis adaptor device which provides time saving and practical means and comforts the wearer.

A still another object of the present invention is to provide disposable venoclysis adaptor device which is simple in design and inexpensive to fabricate. These and other objects of the present invention, which will become apparent hereinafter, are achieved by providing a disposable venoclysis adaptor device including a flexible fastening strap or two of such dimension so as to be temporarily yet firmly secured at a patients limb, two spacing cushions mounted on the fastening strap to keep any pressure off the fluid flow area and an uninterrupted insertion point, and an adaptor pillow to be mounted on the fastening strap between the spacing cushions. An adaptor flap is placed between the spacing cushions, with the adaptor pillow pointing towards the second distance cushion to function as the counterpart of adaptor pillow to sandwich a venotube or butterfly in a substantially fixed position. There are further provided means for securing the fastening straps, means for securing a venotube or butterfly to the disposable venoclysis adaptor device, and a tube flax extending from the joint of the fastening strap so that the extending venotube is fixed in place when patient moves and forces are applied to the venotube.

The novel features of the present invention which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING FIGURES

The figures in the drawings are briefly described as follows:

FIG. 1 is a perspective view of a disposable venoclysis adaptor device according to the invention illustrating its use with closed fastening strap.

FIG. 1A is a perspective view of a restraining attachment.

FIG. 2 is a broken cross sectional view taken along line 2—2 of FIG. 1.

FIG. 3 is a perspective view of the inner side of the adaptor device not in use, showing an open fastening strap and a tube flap.

FIG. 4 is a perspective view of the adaptor device with two fastening straps.

DESCRIPTION OF THE PREFERRED EMBODIMENTS

The disposable venoclysis adaptor device 10 according to the present invention includes a flexible fastening strap 12 forming, as shown in FIG. 1, a loop 18. The fastening strap 12 has a pressure sensitive hook-and-loop type backing and includes, as shown in FIGS. 1 and 2, a strip 14 likewise having a pressure-sensitive backing 16, which is provided at one end of the loop 18 and which is permanently secured to the strap 12. The fastening strap 12 is wrapped around a patient limb. However, it should be understood that any suitable adhering material such as pressure-sensitive adhesive tape ribbon might also be used in place of the strap 12.

The overlapping end of the strip 14 forms a tube flap 22 which receives a tube 52 of a venotube 46 or a butterfly 48 when the tube 52 is placed between a tube flap 22 and the loop 18.

There are provided two spacing cushions 24 having each a hard board back 26 formed as a single layer board. The cushion 24 includes an absorbent padding 28 which absorbs body moisture from the wearer through a woven or non-woven fabric 30. The woven or non-woven fabric 30 is permanently attached to the padding 28 at peripheral edges 32, as shown in FIG. 2.

Needlestripes 58 of rubberized ink printed on the spacing cushions 24 on the surface of the woven or non-woven fabric 30, which contacts the wearer, is to prevent slipping of the adaptor along the wearer's skin.

Two spacing cushions 24 have their hard board backs 26 permanently attached to the fastening strap 12 in the region of the pressure-sensitive adhesive backing 16 of the strip 14 to keep the fastening strap 12 at a distance from the insertion point of the venotube 46 or the butterfly 48 at any applied given area.

An adaptor pillow 34 is placed permanently between the two spacing cushions 24 in the area of the pressure-sensitive adhesive backing 16 of the strip 14 as illustrated in FIGS. 1 and 2. The adaptor pillow 34 is formed of a soft pad 36, which is covered with a fabric mesh 20 provided on the outer side of the soft pad 36. The pad 36 has a film of pressure sensitive adhesive 40 applied to the fabric mesh 30. When not in use, the pressure sensitive adhesive film 40 is covered with a strip of release paper 42 which is pulled off at the time of application.

An adaptor flap 44 of woven or non-woven fabric ribbon material is permanently attached between one spacing cushion 24 and the adaptor pillow 34, pointing at its lose end towards the second spacing cushion 24. The adaptor flap 44 when applied, after the venotube 46 or the butterfly 48 is administered, is slipped under the venotube 46 or the butterfly 48 and is sandwiched by the adaptor pillow 34, which secures the venotube 46 or the butterfly 48 safely at the disposable venoclysis adaptor device 10 which is, then, wrapped around a patient's limb and is secured by the fastening strap 12. The excess tube forms a small loop 50 sandwiched between the tube flap 22 and the loop 18.

An added support of the disposable venoclysis adaptor device 10 at the patient's limb can be provided by a second fastening strap 56 shown in FIG. 4, which is supported by two additional spacing cushions 54, which may be formed, as shown in FIG. 4, as extensions of the cushions 24.

When the adaptor device 10 according to the present invention is used for infants, a single cushion 60, as shown in FIG. 1a is provided. Opposite ends of the strap 12 form a slot 52. The adaptor 10, which is shown in FIG. 1a, has a second strap 64 similar to the strap 12.

What is claimed is:

1. A disposable venoclysis adaptor device for supporting a venotube at a person's limb, said adaptor device comprising:

at least one flexible fastening strap to be secured at the person's limb;

two spacing cushions securable to the strap for eliminating any pressure from a fluid flow area and an insertion point;

an adaptor pillow securable to the strap between the two cushions;

an adaptor flap provided between the cushions and cooperating with the adapter pillow for fixedly retaining a venotube therebetween;

a tube flax provided on the fastening strap for securing an extension of the venotube for preventing displacement of the venotube upon person's limb movement; and means for securing the strap on the person's limb.

2. A disposable venoclysis adaptor devise as set forth in claim 1, wherein the securing means comprises hook and loop fasteners provided at opposite ends of the strap.

3. A disposable venoclysis adaptor device as set forth in claim 1, wherein each of the two spacing cushions has a hard board back fixedly attached to the strap, and an absorbent padding supported on the hard board back.

4. A disposable venoclysis adaptor device as set forth in claim 3, wherein each of the two cushions further comprises a cover formed of one of a woven fabric and a non-woven fabric covering the absorbent padding, and needlestripes provided on the cover on a side thereof spaced from the absorbent padding for applying friction to the person's limb to prevent sliding of the adaptor device on the person's limb.

5. A disposable venoclysis adaptor device as set forth in claim 1, wherein the adaptor pillow is formed of a soft pad provided on a side thereof adjacent to the person's limb with a laminated fabric mesh covered with a release paper strip.

6. A disposable venoclysis adaptor device set forth in claim 1, wherein the adaptor flap is formed of one of a woven fabric ribbon material and a non-woven fabric ribbon material.

7. A disposable venoclysis adaptor device as set forth in claim 1, wherein the tube flax is formed by an extension of the strap extending beyond a connection point of opposite ends of the strap when the strap is secured on the person's limb.

8. A disposable venoclysis adaptor device as set forth in claim 1, further comprising a restraining attachment mounted on the fastening strap when the adaptor device is used for supporting the venotube at a child limb.

* * * * *